United States Patent [19]

Alexander et al.

[11] Patent Number: 4,982,049
[45] Date of Patent: Jan. 1, 1991

[54] PURIFICATION OF HYDROCARBONACEOUS FRACTIONS

[75] Inventors: Richard A. Alexander; Charles E. Knight, both of Mobile, Ala.; Darrell D. Whitehurst, Titusville, N.J.

[73] Assignee: Mobil Oil Corp., New York, N.Y.

[21] Appl. No.: 358,761

[22] Filed: May 26, 1989

[51] Int. Cl.$^5$ .......................... C07C 7/10; C07C 7/12
[52] U.S. Cl. ............................... 585/803; 208/334; 208/335; 208/337; 208/341; 585/352; 585/825; 585/826; 585/867
[58] Field of Search ............... 585/867, 803, 823, 825, 585/826, 352, 350; 208/337, 334, 335, 341, 361, 311

[56] References Cited

U.S. PATENT DOCUMENTS

| | | | |
|---|---|---|---|
| 2,666,500 | 1/1954 | Cahn et al. | 585/823 |
| 3,094,569 | 6/1963 | Thomas | 585/823 |
| 3,567,791 | 3/1971 | Fuller | 585/857 |
| 4,083,772 | 4/1978 | Asselin et al. | 585/857 |
| 4,793,545 | 1/1989 | Schmidt | 585/823 |

OTHER PUBLICATIONS

"Operating Problems in the Hanlan Swan Hills Gas Field" by W. J. King, Presented at the SPE Gas Technology Symposium, Jun. 13–16, 1988, Dallas, Tex.

K. Tominaga et al., "Next Generation Fine Chemicals Raw Material-Adamantane", Chemical Economy & Engineering Review, vol. 17, No. 10, pp. 23–30 (1985).

R. C. Fort, Jr., The Chemistry of Diamond Molecules, Marcel Dekker (1976).

Primary Examiner—Asok Pal
Attorney, Agent, or Firm—Alexander J. McKillop; Charles J. Speciale; Robert B. Furr, Jr.

[57] ABSTRACT

A process for recovering diamondoid compounds from hydrocarbonaceous minerals and/or from deposits left by such minerals in equipment or otherwise, which comprises dissolving diamondoid compounds in an aromatic distillate fuel oil; extracting aromatics from the solution; and separating diamondoid compounds from the raffinate of the extraction.

18 Claims, 5 Drawing Sheets

PURIFICATION OF HYDROCARBONACEOUS FRACTIONS

CROSS REFERENCE TO RELATED APPLICATIONS

The present application is related by the disclosure of similar subject matter to commonly-assigned applications Ser. Nos. 358,758, 358,760, and 358,759, filed concurrently herewith.

BACKGROUND OF THE INVENTION

This invention relates to the removal of certain components from hydrocarbon streams. It more particularly refers to separating diamondoid organic compounds from hydrocarbon streams containing such.

Many hydrocarbonaceous mineral streams contain some small proportion of diamondoid compounds. These high boiling, saturated, three-dimensional polycyclic organics are illustrated by adamantane, diamantane, triamantane and various side chain substituted homologues, particularly the methyl derivatives. These compounds have high melting points and high vapor pressures for their molecular weights and have recently been found to cause problems during production and refining of hydrocarbonaceous minerals, particularly natural gas, by condensing out and solidifying, thereby clogging pipes and other pieces of equipment. For a survey of the chemistry of diamondoid compounds, see Fort, Jr., Raymond C., *The Chemistry of Diamond Molecules*, Marcel Dekker, 1976.

In recent times, new sources of hydrocarbon minerals have been brought into production which, for some unknown reason, have substantially larger concentrations of diamondoid compounds. Whereas in the past, the amount of diamondoid compounds has been too small to cause operational problems such as production cooler plugging, now these compounds represent both a larger problem and a larger opportunity. The presense of diamondoid compounds in natural gas has been found to cause plugging in the process equipment requiring costly maintenance downtime to remove. On the other hand, these very compounds which can deleteriously affect the profitability of natural gas production are themselves valuable products.

BROAD STATEMENT OF THE INVENTION

According to this invention, it has now been found that diamondoid compounds may be extracted from hydrocarbonaceous gas streams by contacting the gas stream with an aromatic distillate in which diamondoid compounds are at least partially soluble. It has been found that the diamondoid compounds are preferentially dissolved from the gas stream into an aromatic distillate thereby providing a method not only for preventing or reducing plugging of downstream process equipment but also for recovering valuable diamondoid compounds. Aromatic distillates useful in the solvation process of the invention include normally liquid hydrocarbons containing aromatics including petroleum-based solvents such as kerosene, diesel fuel, and heavy gasoline, with diesel fuel being the most preferred aromatic distillate.

Further, it has been found that a second separation step, silica gel sorption, is effective to sorb diamondoid compounds from a hydrocarbon gas stream. Depending upon the composition of the hydrocarbon gas stream, aromatic distillate addition may optionally be employed to reduce diamondoid deposition in the silica gel sorption equipment, with aromatic distillate injection to the silica gel regeneration circuit as described below being particularly beneficial.

Both diamondoid separation steps are employed in the preferred embodiment of the invention. The diamondoid compound-containing hydrocarbon gas stream is first contacted with a suitable aromatic distillate as described above. The gas/liquid mixture is then separated, e.g. flashed, to form an at least partially purified gas stream and a liquid aromatic distillate stream enriched in diamondoid compounds. If the diamondoid compound-containing gas stream to be purified is rich in substituted higher boiling point adamantane homologues, the solvation and gas/liquid separation steps may produce a gas stream having acceptable purity. If, however, if the diamondoid compound-containing gas feedstream contains a substantial fraction of less substituted lower boiling point adamantane homologues, the silica gel sorption step may be necessary to achieve the desired gas product stream purity or extent of diamondoid recovery.

The present invention, then, provides a solvation process for extracting diamondoid compounds from a gas stream comprising the steps of providing a gas stream containing a recoverable concentration of diamondoid compounds, mixing the gas stream containing diamondoid compounds with an aromatic distillate in which diamondoid compounds are at least partially soluble, controlling the conditions including temperature and pressure of the mixture to maintain at least a portion of the mixture in the liquid phase, separating the mixture under these controlled conditions into a vapor stream and a diamondoid-enriched aromatic distillate stream, and recovering diamondoid compounds from the diamondoid-enriched aromatic distillate stream by extracting the diamondoid-enriched aromatic distillate stream with an aromatics selective solvent to produce at least a diamondoid rich raffinate and an aromatics rich extract; and recovering diamondoid compounds from the diamondoid rich raffinate.

The invention further provides a sorption process for extracting diamondoid compounds from a diamondoid-containing gas stream comprising the steps of providing a gas stream containing a recoverable concentration of diamondoid compounds, contacting the diamondoid-containing gas stream with silica gel in a sorption zone under conditions of temperature and pressure to prevent substantial formation of solid diamondoid desposits in the sorption zone for a period of time sufficient for the silica gel to sorb at least a portion of the diamondoid compounds from the hydrocarbon gas, regenerating the silica gel by contacting the silica gel with a regeneration fluid in which diamondoid compounds are at least partially soluble to desorb diamondoid compounds from the silica gel, separating the regeneration fluid into a regeneration gas stream and a regeneration liquid stream, and concentrating diamondoid compounds in the regeneration liquid stream by a method which comprises extracting the regeneration liquid stream with an aromatics selective solvent to produce at least a diamondoid rich raffinate and an aromatics rich extract, and recovering diamondoid compounds from the diamondoid rich raffinate.

The preferred embodiment of the invention includes both the solvation and sorption stages, providing a process for extracting diamondoid compounds from a diamondoid-containing gas stream comprising the steps of providing a gas stream containing a recoverable concentration of diamondoid compounds, mixing the gas stream containing diamondoid compounds with an aromatic distillate in which diamondoid compounds are at least partially soluble, controlling the conditions including temperature and pressure of the mixture to maintain at least a portion of the mixture in the liquid phase, separating the mixture under the controlled conditions into a partially purified gas stream and a diamondoid-enriched aromatic distillate stream, recovering diamondoid compounds from the diamondoid-enriched aromatic distillate stream, recovering diamondoid compounds from the diamondoid-enriched aromatic distillate stream by extracting the diamondoid-enriched aromatic distillate stream with an aromatics selective solvent to produce at least a diamondoid rich raffinate and an aromatics rich extract; and recovering diamondoid compounds from the diamondoid rich raffinate, contacting the partially purified gas stream with silica gel in a first sorption zone under conditions of temperature and pressure to prevent substantial formation of solid diamondoid desposits in the sorption zone for a period of time sufficient for the silica gel to sorb at least a portion of the diamondoid compounds from the hydrocarbon gas, recovering diamondoid compounds from silica gel by desorption in a second sorption zone by contacting the silica gel with a regeneration fluid in which diamondoid compounds are at least partially soluble to desorb diamondoid compounds from the silica gel, separating the regeneration fluid into a regeneration gas stream and a regeneration liquid stream, concentrating diamondoid compounds in the regeneration liquid stream by extracting the regeneration liquid stream with an aromatics selective solvent to produce at least a diamondoid rich raffinate and an aromatics rich extract, and recovering diamondoid compounds from the diamondoid rich raffinate.

According to this invention, diamondoid compounds contained in an aromatic fraction can be concentrated by solvent extraction, not of the diamondoid compounds, but of the aromatics into which they have been dissolved and with which they are admixed. Thus these aromatics can be taken away leaving the bulky, saturated diamondoid compounds as a raffinate in admixture with other aliphatic compounds, most of which are saturated and substantially linear.

It has been found that this raffinate stream can be subjected to further resolution to separate the diamondoid compounds from the linear aliphatics.

The extract stream is suitably resolvable to separate the extracting solvent from the aromatics separated from the diamondoid compounds in the extraction step. This separation can be accomplished by distillation, whereupon the extracting solvent can be recycled for further use as an extractant, and the aromatic fraction can be recycled for further use in washing diamondoid compounds from additional hydrocarbonaceous source and from the production and/or refining equipment.

SPECIFIC EMBODIMENTS OF THIS INVENTION

For the purposes of clarity, the petroleum-based solvents useful to extract diamondoid compounds from a hydrocarbon gas stream will be referred to generically as aromatic distillate, as opposed to aromatics extraction solvents such as furfural which are referred to generically herein as extraction solvent.

Figure 1:
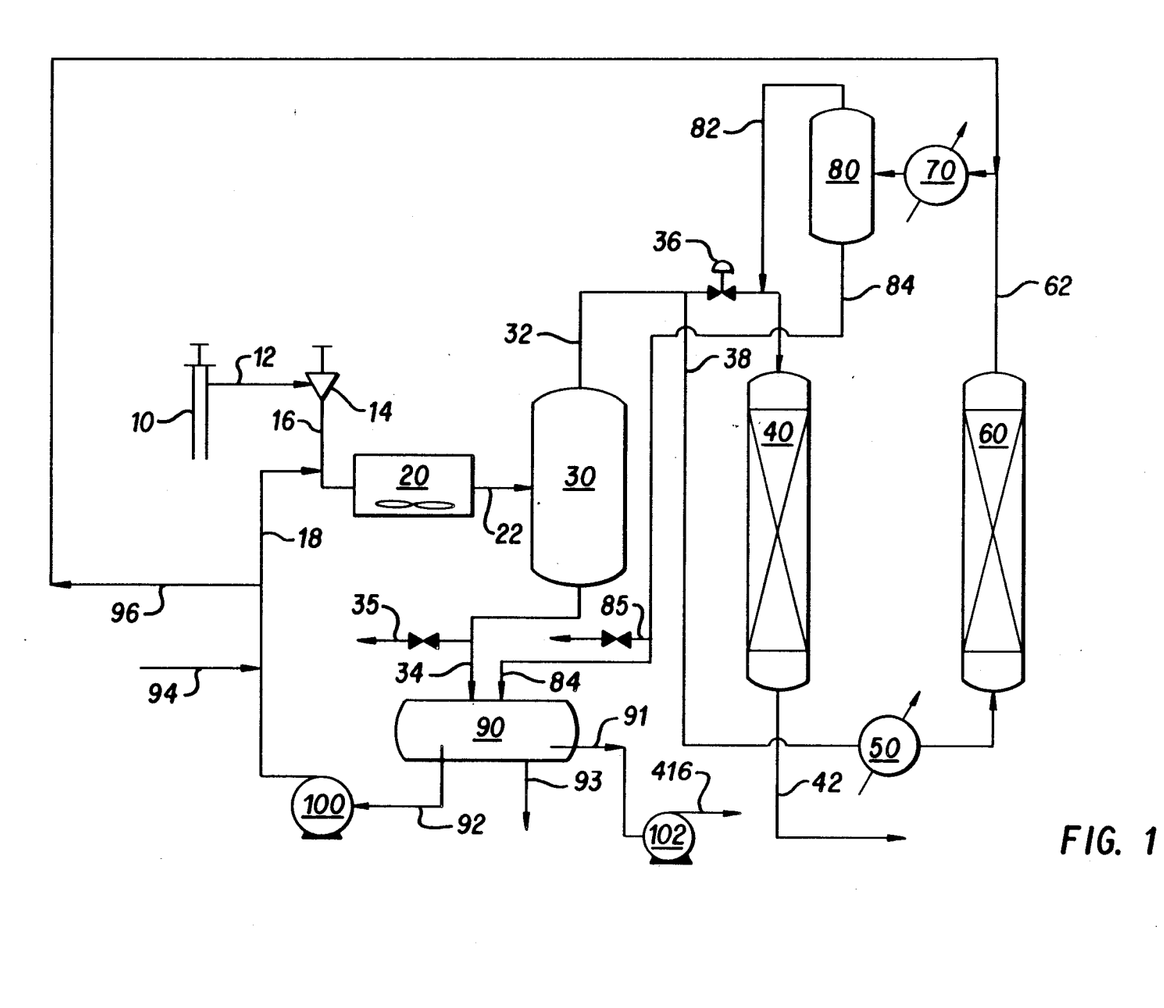
FIG. 1 is a simplified schematic showing major processing steps of a preferred embodiment of the invention.

Referring now to FIG. 1, a preferred embodiment of the present invention is schematically illustrated. A diamondoid-laden natural gas stream 12 is withdrawn from wellhead 10 at high pressure, generally between about 3000 and 15,000 psig, typically around 11,000 psig. Pressure reduction valve 14, commonly referred to as a choke, reduces the natural gas pressure downstream of the choke to between about 900 and about 1400 psig. Recycled aromatic distillate 18 is injected into the reduced pressure diamondoid-laden natural gas stream 16 upstream of process cooler 20 to prevent deposition of diamondoid solids within the cooler. Process cooler 20 is typically an air cooled exchanger with extended heat exchange tube surface area, commonly known as a fin-fan exchanger.

Aromatic distillate injection rates of about 2 to 6 gallons per minute (GPM) at natural gas flowrates of 10 to 15 million standard cubic feet per day (MMSCF/D) have been found to be effective to reduce diamondoid deposition. Thus to achieve the desired diamondoid sorption in the added aromatic distillate, aromatic distillate charge rates of about 100 to 1000 gallons per million standard cubic feet of natural gas (G/MMSCF) are acceptable, and rates of between about 200 and 800 G/MMSCF are preferred. The optimum charge rate within the disclosed ranges to minimize aromatic distillate costs while preventing diamondoid deposition in the downstream process equipment may be determined by one of ordinary skill in the art with a reasonable amount of trial and error.

If the aromatic distillate dosage selected for process operation is insufficient to maintain the diamondoids in solution through the process cooler, or if aromatic distillate injection is temporariliy discontinued for operational reasons such as injection pump failure, diamondoids will likely be deposited on the inner surfaces of the process cooler heat exchange tubes, increasing the pressure drop across the air cooled exchanger. Thus one recommended method for determining optimum aromatic distillate dosage would be to monitor the change in natural gas pressure ($\Delta P$) across the process cooler with respect to time. An decrease in the $\Delta P$ across the process cooler would likely indicate diamondoid deposition on the inner surfaces of the cooler tubes and could be corrected with increased aromatic distillate dosage. The technique of monitoring heat exchanger operation by evaluating $\Delta P$ over time is well known to those skilled in the art of heat exchanger design and maintenance.

Depending on the concentration of diamondoid compounds in the natural gas stream as well as on the operating temperature and pressure, discontinuation of the aromatic distillate charge may precipitate partial or complete plugging of at least a portion of the process cooler heat exchange tubes. Such deposits may be removed via intermittent high dosage or "slug" aromatic distillate treatment. Slug aromatic distillate treatment has been found to be effective for removing diamondoid deposits from process cooler heat exchange tubes, e.g., charging 50 to 100 gallon slugs of aromatic distillate intermittently into the 10 to 15 MMSCF/D natural gas stream at a point upstream of the process cooler. The slugged aromatic distillate is then recovered by a method similar to that used for the continuously injected aromatic distillate, which method is described below.

The cooled mixture of natural gas and aromatic distillate 22 flows to production separator 30 where it is flashed to form an overhead vapor stream 32 and a bottom liquid stream 34. Production separator 30 is illustrated as a flash drum, i.e. a single stage vapor-liquid separation device, but may also comprise any suitable vapor-liquid separation apparatus known to those skilled in the art of process equipment design.

A first portion of the overhead vapor stream 32 flows through control valve 36 to enter sorption zone 40 while a second portion of the overhead vapor stream flow is preferably diverted by control valve 36 to form regeneration gas stream 38. The total overhead vapor stream may be charged to the sorption zone if an inert gas stream for use as a regeneration gas is both inexpensive and easily piped into the sorption process equipment. It is generally preferred, however, to use a portion of the overhead vapor stream as a regeneration gas due to its inherent economy and availability. Regeneration gas flow to the silica gel sorption zone is preferably countercurrent, i.e., gas flow for silica gel desorption during regeneration should be oriented in the opposite direction from gas flow for silica gel sorption during gas purification operation.

The first portion of the overhead vapor stream 32 then contacts a silica gel sorbent contained in sorption zone 40. The overhead vapor stream preferably flows downwardly in contact with the silica gel sorbent throught the length of the sorption zone 40. Silica gel volume is preferably selected such that almost all of the silica gel sorption capacity is utilized before regeneration.

The purified gas stream 42 is then withdrawn from sorption zone 40 and charged to pipeline or storage facilities. The second portion of the overhead vapor stream is preferably diverted for use as a regeneration gas as described above. Part of the purified gas stream 42 may be compressed and heated for use as a regeneration gas (compression equipment not shown). Generating silica gel using the purified gas effluent, for example from sorption zone 40, may prolong the silica gel useful life by decreasing the rate of steam deactivation. Regeneration gas 38 is heated in regeneration heat exchanger 50 to a temperature less than 315° C. (600° F.), preferably between about 177° and 288° C. (350° and 550° F.) and then charged to the bottom of sorption zone 60 to countercurrently desorb water and heavy hydrocarbons, particularly diamondoids, from the silica gel. The length of the regeneration step is a function of regeneration gas temperature and flowrate as well as the amount of sorbed material contained in the silica gel sorption bed. These operating parameters may be varied to synchronize the regeneration cycle (desorption) of a first sorption zone with the gas purification cycle (sorption) of a second sorption zone. The sorption zones are preferably piped and valved in a parallel configuration such that one sorption zone may be operated in the gas purification mode while the other sorption zone is countercurrently regenerated.

Enriched regenerated gas 62 is cooled to a temperature of between about 24° and 60° C. (75° and 140° F.) in regeneration cooler 70 and is flashed in regeneration separator 80 to form a overhead gas stream 82 and a liquid bottom stream 84. The overhead gas stream is preferably recycled and mixed with the production separator overhead stream and purified in sorption zone 40. The regeneration separator overhead gas stream 82 may optionally be mixed with purified gas stream 42. While such optional configuration beneficially reduces the total gas flow through the sorption zone operating in the gas purification mode, it necessarily reduces both diamondoid compound recovery and natural gas product purity.

Liquid bottom stream 34 from production separator 30 and 84 from regeneration separator 80 normally flow to aromatic distillate accumulator drum 90. A portion of the diamondoid-containing aromatic distillate 91 is drawn off the aromatic distillate accumulator and purified to maintain diamondoid concentration in the aromatic distillate below saturation. A water stream 93 is drawn off from aromatic distillate accumulator drum 90 and is sent to the process sewer for treatment and hydrocarbon recovery. The remaining diamondoid-containing aromatic distillate 92 is withdrawn from aromatic distillate accumulator drum 90, charged through pump 100 and mixed with purified aromatic distillate 94 to form recycled aromatic distillate stream 18 which is added to the natural gas stream 16 upstream from process cooler 20 as described above.

A slip stream of diamondoid-containing aromatic distillate 96 may optionally be diverted from recycled aromatic distillate stream 18 and mixed with the enriched regeneration gas stream 62 upstream of regeration cooler 70. This slip steam addition to the enriched regeneration gas stream may be necessary to avoid diamondoid deposition in the regeneration gas cooler.

If the diamondoids contained in the feedstream to the present process consist predominately of adamantane and diamantane, it has been found that the two compounds may be effectively segregated and recovered separately. Given a feedstream in which the diamondoids principally consist of adamantane and diamantane, the liquid bottom streams from the production separator 30 and regeneration separator 80 have been found to be rich in diamantane and adamantane, respectively. Thus to recover the two compounds at relatively high purity, streams 35 and 85 are drawn off of streams 34 and 84, respectively, and are routed to separate diamondoid recovery processes (not shown).

The foregoing process description exemplifies one method by which a diamondoid-containing aromatic distillate may be obtained for subsequent concentration by aromatics extraction as described below. The following process description details the steps by which a diamondoid-containing aromatic distillate stream may be treated to provide a stream rich in diamondoid compounds which may then be more easily purified to recover diamondoids.

Figure 2:
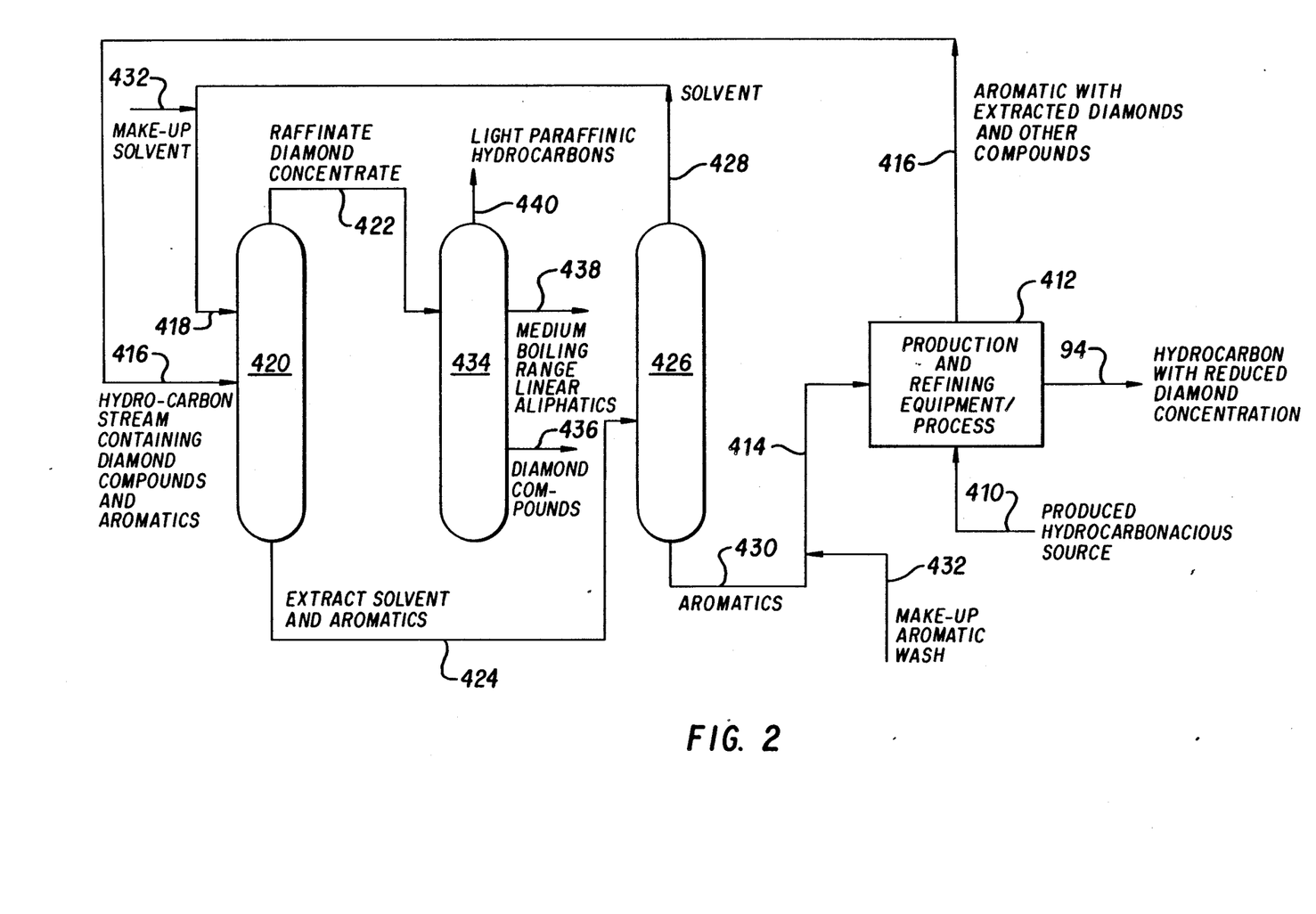
FIG. 2 is a block flow diagram illustrating the aromatics-selective solvent extraction aspects of the invention.

Referring now to the FIG. 2, a hydrocarbonaceous mineral source, or fraction thereof, such as natural gas, 410 is fed into a production/refining processing system 412. The hydrocarbonaceous mineral source is most preferably a diamondoid-laden natural gas stream as designated by numeral 12 in FIG. 1, described above. The production/refining processing system described with reference to FIG. 1 is a preferred embodiment of the production/refining processing system designated by numeral 412 in FIG. 2.

As part of this processing, the equipment may periodically be treated with an aromatic distillate 414 as described above with reference to FIG. 1. The hydrocarbon source 410 is preferably subjected to continuous washing with the aromatic distillate as described above. This washing/extraction process produces an extract 416 comprising diamondoid compounds, aromatic compounds not readily separable from the diamondoid compounds by distillation, linear aliphatic compounds and other compounds. The diamondoid compound containing stream 416 is then contacted with an aromatic-selective solvent feed 418 in an extraction zone 420 under extraction conditions so as to partition the aromatics away from the diamondoid compounds and produce a diamondoid rich, substantially aliphatic raffinate 422 and an aromatics rich, solvent extract 424.

The extract stream 424 is fed to a distillation column 426 which separates the stream into an aromatics-selective solvent distillate 428, and an aromatics-rich raffinate 430. The aromatics-rich raffinate 430 may have make-up aromatic distillate 432 added thereto if needed to reconstitute the aromatic distillate 414. The aromatics selective solvent 428 has make-up solvent 432 added thereto if needed to reconstitute the aromatic selective solvent feed 418.

The diamondoid containing raffinate 422 from the solvent extraction zone 420 is suitably fed to a distillation column 434 where it is resolved into a raffinate 436 rich in diamondoid compounds and other streams 438 and 440 rich in aliphatics of different boiling ranges. This invention is concerned with the production and recovery of the diamondoid compound fraction of the original hydrocarbonaceous feed. The recovery distillate streams 438 and 440 are merely illustrative of some other fractions which can be recovered in this distillation step. It is readily apparent that the number and content of the various distillate streams from this particular operation will be a function of the content of the feed and the particular product needs of the refiner.

The solvent extraction operation of this invention is itself a well known petroleum and petrochemical unit operation. Its application to the particularly described service constitutes an important part of this invention. Aromatic-selective solvents are well known and are illustrated by furfural, sulfolane, phenol, duosol, dimethyl formamide, etc. There are several well known commercially practiced and available aromatics extraction processes, such as Udex, which may be quite suitable for use in this service.

One particularly important feature and attribute of this invention concerns corrosion inhibiting additives which are conventionally added to the distillate fuel oil wash liquid used to keep the producing and refining system clean of plugging deposits. It has quite surprisingly been found, much to the refiner's advantage, that the corrosion inhibitors frequently used in this service are recovered as a direct consequence of the aromatics extraction operation used herein. Thus it has been found that in extracting aromatics from admixture with diamondoids and other saturated organics, the corrosion inhibitors partition with the aromatics and are thereby separated and recovered from the diamondoid rich raffinate. Further, it has most advantageously been found that these corrosion inhibitors stay with the aromatics when the extract phase is later subjected to further resolution to separate the extracting solvent, sulfolane for example, from the aromatics rich distillate fuel oil. Thus these expensive corrosion inhibitors continually recycle through the system along with the aromatics. Make-up may be required from time to time. However, the process hereof saves and reuses large proportions of aromatic distillate-soluble corrosion inhibitors as opposed to the prior art practice of burning them along with the distillate fuel or solvent.

One example of an aromatic-distillate soluble corrosion inhibitor which is commonly used in this service is KP-151 brand corrosion inhibitor distributed by the Petrolite Company of St. Louis, Mo.

According to this invention, the aromatics extraction step is suitably carried out with solvent used in excess, with respect to the stream being extracted, of about 2 to 1 to 5 to 1 ratio. Even higher excess solvent can be used. The particular solvent chosen for the extraction must be a good solvent for aromatic hydrocarbons and a poor solvent for saturated hydrocarbons. The solvent should preferably have a boiling point lower than the boiling point of the aromatics being extracted and preferably should not form an azeotrope with any of them.

The extraction temperature is suitably about 35° to 200° C., (95° to 392° F.), preferably about 60° to 100° C., (140° to 212° F.). The temperature of the extraction process, and indeed the solvent to feed ratio, may be tailored to suit the particular type of operation preferred in any specific situation. It is usually preferred to run the extraction process at as high a temperature as possible, consistent with other operating limitations, in order to induce rapid equilibration of the feed and to prevent or at least retard crystallization of the high melting diamondoids, particularly as their concentration increases as the aromatics are extracted away. However temperatures below the normal boiling point of the extraction solvent are preferred in order to avoid excessive pressures during the extraction process. Pressure is suitably controlled to maintain the aromatics extraction solvent and the aromatic distillate in the liquid phase at operating temperature, typically between atmospheric pressure and about 790 kPa (100 psig).

The temperature, pressure and ratio of solvent to feed all can be interdependently varied to adjust the proportion of diamondoids being recovered. Thus if it is desired to recover the most diamondoids possible from the feed, the temperature will be kept to a minimum consistent with all of the other parameters hereof, and the proportion of solvent will be kept toward the lower end of the range specified. To the contrary, when it is desired to operate this process to maximize throughput and merely to keep the production/refining equipment clean and unplugged, higher temperatures and higher extractant ratios will be used. In this way, although lower proportions of diamondoids will be recovered, the process can be operated with higher throughputs and a good equilibrium of diamondoid concentration can be achieved sufficient to minimize plugging problems.

The extract phase from the aromatics extraction process is suitably resolved by fractional distillation in any conventional distillation column suitably designed to separate the extracting solvent from the aromatics/corrosion inhibitor extract. If the boiling points are far enough apart, flashing may be sufficient.

The raffinate, containing the diamondoid compound to be recovered, may also be resolved by distillation or steam stripping such that the diamondoids are recovered as raffinate. The type of distillation and the perfection of partition (recovery) is a matter of choice and design. Clearly the distillation operating parameters which will yield the largest diamondoid recovery will probably also yield the least pure diamondoid product. The contrary is also true, vis: a purer diamondoid product stream will be achieved at the expense of the quantity recovered. If desired, a train of distillation means can be suitably used.

SPECIFIC EXAMPLES

In all of the examples, parts and percentages are by volume unless expressly stated to be on some other basis.

Figure 3:
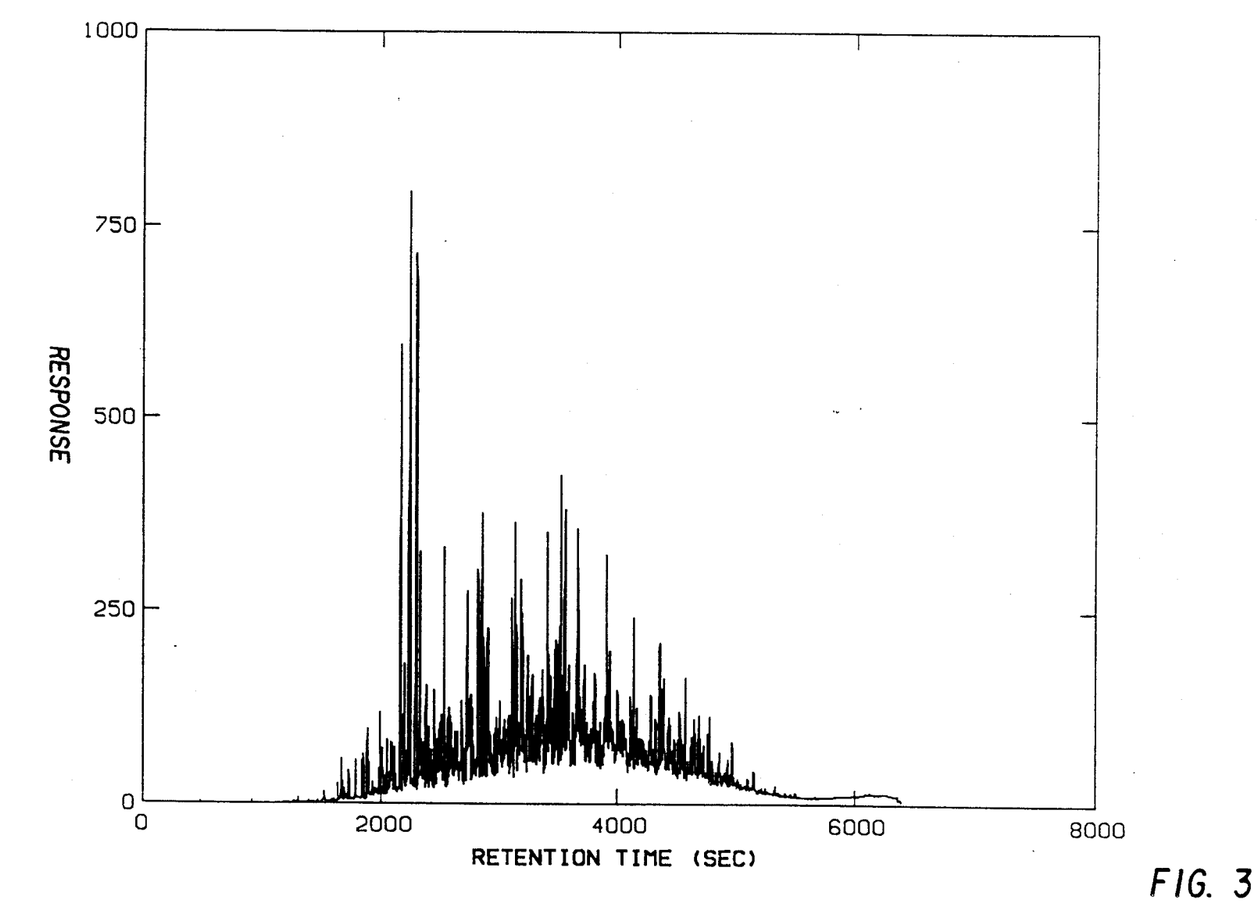
FIGS. 3, 4, and 5 are gas chromatographic analyses.

In the following examples a mixture of an equilibrium mixture of 10 parts of diamondoids dissolved in 90 parts of an aromatic distillate fuel oil containing 0.8 wt. % of KW-111 brand carboxylic acid/polyamine antifoam and 400 ppm wt. of KP-151 brand thioalkyl substituted phenolic heterocyclic corrosion inhibitor was used. The antifoam and corrosion inhibitor were purchased from the Petrolite Company of St. Louis, Mo. The aromatic distillate fuel oil was a diesel fuel having an approximate composition as shown in the following Table. FIG. 3 shows a gas chromatographic analysis of the feed material.

| Aromatics | 46–58 wt. % |
| --- | --- |
| Paraffins | 22–29 wt. % |
| 1-ring Naphthenes | 12–18 wt. % |
| 2-ring Naphthenes | 5–6 wt. % |
| 3-ring Naphthenes | 1–3 wt. % |

EXAMPLE I

Three hundred (300) parts of the feed mixture identified above was extracted with 600 parts of furfural at room temperature and atmosphere pressure in a batch extraction. After the mixture was shaken, and partitioned itself into layers, an additional 100 parts of furfural were added and the upper layer further extracted thereby. The saturated hydrocarbon (upper) layer was decanted off, washed with a mixture of 1 part methanol and 3 parts water to remove any lingering furfural, and then dried over alumina to yield 100 parts of diamondoid containing product.

The diamondoid containing product was resolved into its components in a gas chromatograph which analyzed the product to contain 15 parts of diamondoid. While the extract phase was not further resolved, it could have been conventionally separated to recover and recycle the furfural.

Figure 4:
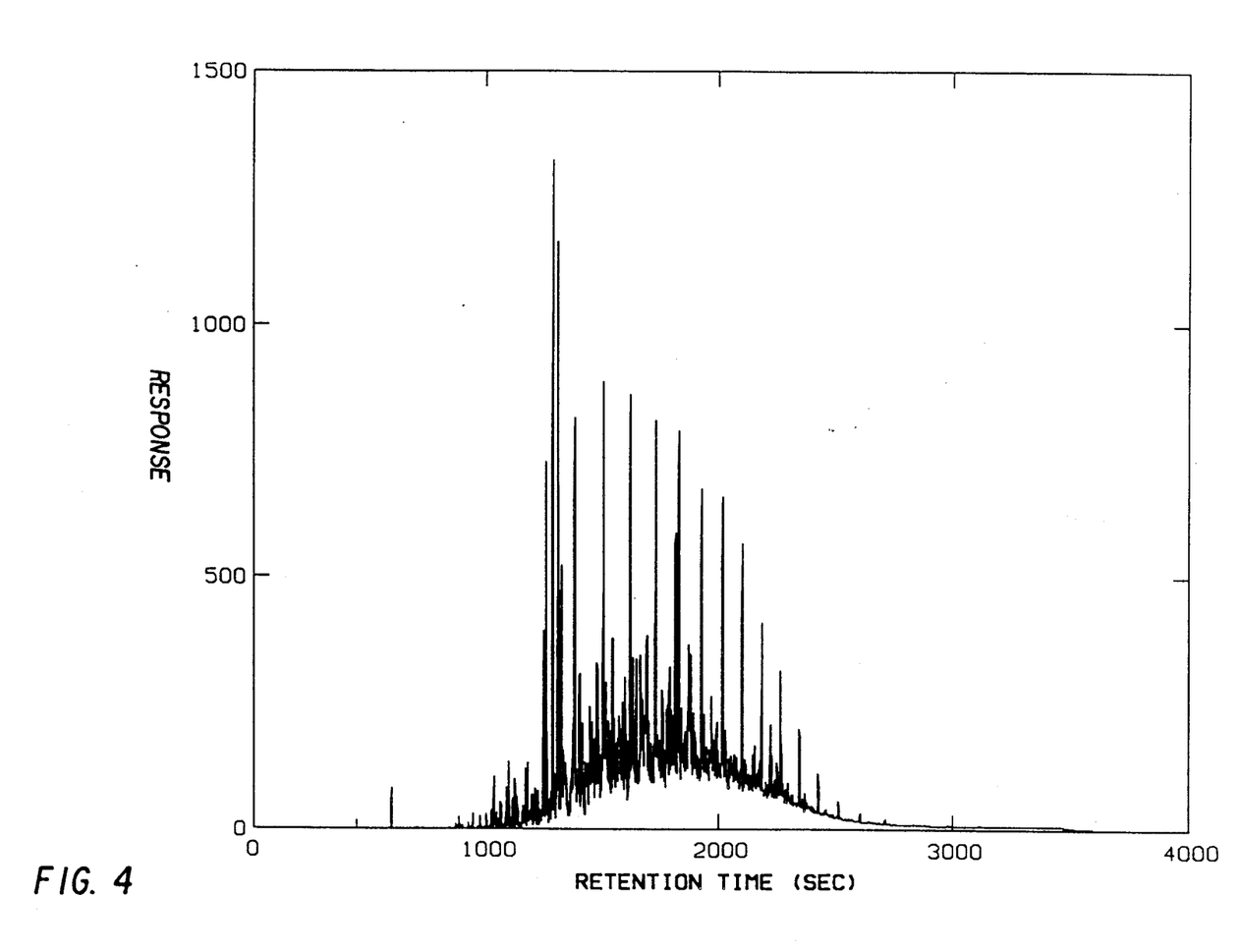

FIG. 4 shows a gas chromatographic analysis of the raffinate from the extraction unit.

EXAMPLE II

This example was run on the same feed mixture as in Example I. About 30 parts of feed was extracted with 100 parts of dimethyl formamide at room temperature. The raffinate was subjected to gas chromatographic separation to show a yield of about 15 parts of diamondoids.

Figure 5:
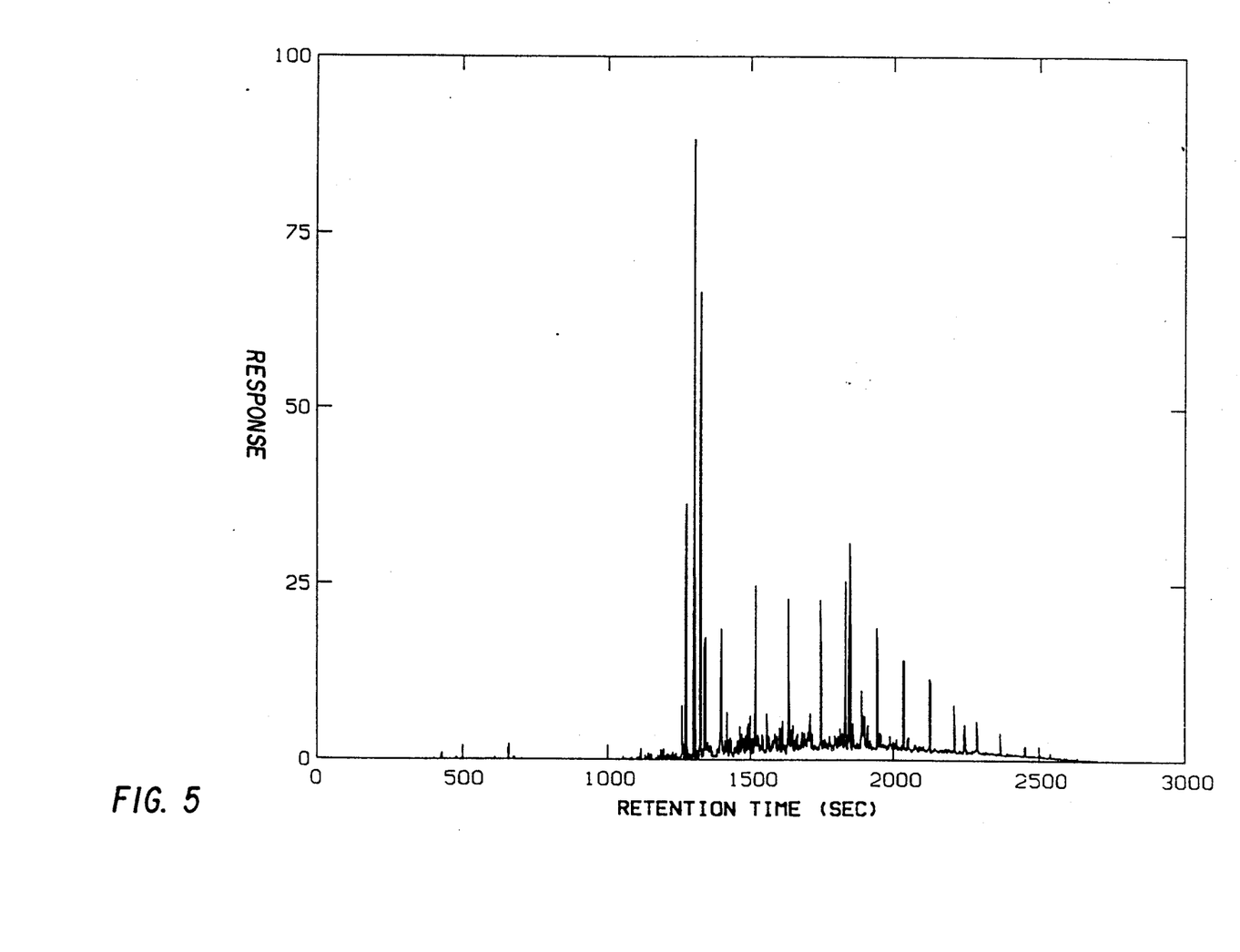

FIG. 5 shows a gas chromatographic analysis of the raffinate from the extraction unit.

Changes and modifications in the specifically described embodiments can be carried out without departing from the scope of the invention which is intended to be limited only by the scope of the appended claims.

What is claimed is:

1. A process for concentrating diamondoid compounds in a substantially hydrocarbon solution thereof containing aromatic fractions which comprises extracting said solution with an aromatics selective solvent to produce at least a diamondoid rich raffinate and an aromatics rich extract; and recovering diamondoid compounds from said diamondoid rich raffinate.

2. A process as claimed in claim 1 wherein said diamondoid compounds are substantially unseparable from at least the aromatics fraction of said hydrocarbon solution thereof by distillation.

3. A process as claimed in claim 1 wherein said aromatics selective solvent is at least one selected from the group consisting of furfural, sulfolane, phenol, duosol and dimethyl formamide.

4. The process claimed in claim 1 wherein said extraction is carried out at about 35° to 200° C. (95° to 392° F.).

5. The process claimed in claim 1 wherein said extraction is carried out at an extractant to substantially hydrocarbon solution ratio of about 2 to 1 to 5 to 1.

6. The process claimed in claim 1 wherein said substantially hydrocarbon solution further contains at least one corrosion inhibitor.

7. The process claimed in claim 6 wherein said extraction partitions said corrosion inhibitor with said aromatics and away from said diamondoid compounds.

8. The process claimed in claim 1 including separating said extract fraction into extractive solvent fraction and aromatics rich fraction and recycling said extractive solvent.

9. A process comprising contacting a substantially hydrocarbonaceous mineral containing diamondoid compounds with an aromatic rich distillate fuel oil, whereby transporting diamondoid compounds from said mineral to said oil; extracting said oil/diamondoid fraction with an aromatics selective solvent under conditions adapted to form an aromatics rich extract and a diamondoid compound rich raffinate; and separating diamondoid compounds from said raffinate.

10. The process claimed in claim 9 wherein said solvent comprises furfural, sulfolane, phenol, duosol, dimethyl formamide or mixtures thereof.

11. The process claimed in claim 9 wherein said diamondoid compounds are separated from said raffinate by gas chromatography.

12. A process for extracting diamondoid compounds from a gas stream comprising the steps of:
  (a) providing a gas stream containing a recoverable concentration or diamondoid compounds;
  (b) mixing said gas stream containing diamondoid compounds with a solvent in which diamondoid compounds are at least partially soluble;
  (c) controlling the conditions including temperature and pressure of said mixture of step (b) above to maintain at least a portion of said mixture in the liquid phase;
  (d) separating said mixture under the controlled conditions of step (c), above into a vapor stream and a diamondoid-enriched solvent stream; and
  (e) recovering diamondoid compounds from said diamondoid-enriched solvent stream by extracting said diamondoid-enriched solvent stream with an aromatics selective solvent to produce at least a diamondoid rich raffinate and an aromatics rich extract; and recovering diamondoid compounds from said diamondoid rich raffinate.

13. The process of claim 12 wherein said gas stream comprises natural gas.

14. The process of claim 12 wherein step (d) further comprises cooling said mixture of step (c).

15. The process of claim 14 wherein said cooling step comprises reducing the temperature of said mixture of step (c) to a temperature between about 24° and 60° C. (75° and 140° F.).

16. A process for extracting diamondoid compounds from a diamondoid-containing gas stream comprising the steps of:
   (a) providing a gas stream containing a recoverable concentration of diamondoid compounds;
   (b) contacting said diamondoid-containing gas stream with silica gel in a sorption zone for a period of time sufficient for said silica gel to sorb at least a poriton of said diamondoid compounds from said hydrocarbon gas;
   (c) regenerating said silica gel by contacting said silica gel with a regeneration fluid in which diamondoid compounds are at least partially soluble to desorb diamondoid compounds from said silica gel;
   (d) separating said regeneration fluid into a regeneration gas stream and a regeneration liquid stream; and
   (e) concentrating diamondoid compounds in said regeneration liquid stream by a method which comprises extracting said regeneration liquid stream with an aromatics selective solvent to produce at least a diamondoid rich raffinate and an aromatics rich extract; and recovering diamondoid compounds from said diamondoid rich raffinate.

17. The process of claim 16 wherein said silica gel contacting step (b) is carried out under conditions of temperature and pressure to prevent substantial formation of solid diamondoid desposits in said sorption zone 18. A process for extracting diamondoid compounds from a diamondoid-containing gas stream comprising the steps of:
   (a) providing a gas stream containing a recoverable concentration of diamondoid compounds;
   (b) mixing said gas stream containing diamondoid compounds with a solvent in which diamondoid compounds are at least partially soluble;
   (c) controlling the conditions including temperature and pressure of said mixture of step (b) above to maintain at least a portion of said mixture in the liquid phase;
   (d) separating said mixture under the controlled conditions of step (c), above into a partially purified gas stream and a diamondoid-enriched solvent stream;
   (e) recovering diamondoid compounds from said diamondoid-enriched aromatic distillate stream by extracting said diamondoid-enriched aromatic distillate stream with an aromatics selective solvent to produce at least a diamondoid rich raffinate and an aromatics rich extract; and recovering diamondoid compounds from said diamondoid rich raffinate;
   (f) contacting said partially purified gas stream with silica gel in a first sorption zone for a period of time sufficient for said silica gel to sorb at least a poriton of said diamondoid compounds from said hydrocarbon gas;
   (g) recovering diamondoid compounds from silica gel in a second sorption zone by contacting said silica gel with a regeneration fluid in which diamondoid compounds are at least partially soluble to desorb diamondoid compounds from said silica gel;
   (h) separating said regeneration fluid into a regeneration gas stream and a regeneration liquid stream; and
   (i) concentrating diamondoid compounds in said regeneration liquid stream by a method which comprises extracting said regeneration liquid stream with an aromatics selective solvent to produce at least a diamondoid rich raffinate and an aromatics rich extract; and recovering diamondoid compounds from said diamondoid rich raffinate.

* * * * *

UNITED STATES PATENT AND TRADEMARK OFFICE
CERTIFICATE OF CORRECTION

PATENT NO. : 4,982,049

DATED : January 1, 1991

INVENTOR(S) : Richard A. Alexander et al.

It is certified that error appears in the above-identified patent and that said Letters Patent is hereby corrected as shown below:

```
Col. 11, line 17, "poriton" should be --portion--.
Col. 11, line 38, "desposits" should be --deposits--.
Col. 12, line 23, "poriton" should be --portion--.
```

Signed and Sealed this

Thirtieth Day of June, 1992

Attest:

DOUGLAS B. COMER

Attesting Officer

Acting Commissioner of Patents and Trademarks